US011572456B2

(12) United States Patent
Chen

(10) Patent No.: US 11,572,456 B2
(45) Date of Patent: Feb. 7, 2023

(54) POLYVINYL ALCOHOL COMPOSITION, PREPARATION METHOD THEREOF, AND POLYVINYL ALCOHOL MEDICAL CATHETER CONTAINING THEREOF

(71) Applicant: Xiamen Sibikon New Material Co., Ltd., Fujian (CN)

(72) Inventor: Shaoyong Chen, Fujian (CN)

(73) Assignee: Xiamen Sibikon New Material Co., Ltd., Fujian (CN)

( * ) Notice: Subject to any disclaimer, the term of this patent is extended or adjusted under 35 U.S.C. 154(b) by 518 days.

(21) Appl. No.: 16/862,580

(22) Filed: Apr. 30, 2020

(65) Prior Publication Data

US 2020/0270427 A1 Aug. 27, 2020

Related U.S. Application Data

(63) Continuation of application No. PCT/CN2018/074374, filed on Jan. 27, 2018.

(30) Foreign Application Priority Data

Jan. 15, 2018 (CN) .................. 201810036428.X

(51) Int. Cl.
| | |
|---|---|
| *C08K 13/02* | (2006.01) |
| *C08J 7/04* | (2020.01) |
| *A61L 29/04* | (2006.01) |
| *A61L 29/08* | (2006.01) |
| *C08F 16/06* | (2006.01) |
| *C08J 3/22* | (2006.01) |
| *C08K 3/16* | (2006.01) |
| *C08K 5/053* | (2006.01) |
| *C08K 5/07* | (2006.01) |
| *C08K 5/09* | (2006.01) |
| *C08K 5/21* | (2006.01) |
| *B29C 48/00* | (2019.01) |
| *B29C 48/09* | (2019.01) |
| *B29K 29/00* | (2006.01) |
| *B29L 31/00* | (2006.01) |

(52) U.S. Cl.
CPC ............ *C08K 13/02* (2013.01); *A61L 29/041* (2013.01); *A61L 29/08* (2013.01); *C08F 16/06* (2013.01); *C08J 3/226* (2013.01); *C08J 7/0427* (2020.01); *C08K 3/16* (2013.01); *C08K 5/053* (2013.01); *C08K 5/07* (2013.01); *C08K 5/09* (2013.01); *C08K 5/21* (2013.01); *B29C 48/022* (2019.02); *B29C 48/09* (2019.02); *B29K 2029/04* (2013.01); *B29L 2031/7542* (2013.01); *C08J 2329/04* (2013.01); *C08J 2439/06* (2013.01); *C08K 2003/162* (2013.01); *C08K 2201/014* (2013.01)

(58) Field of Classification Search
CPC .......... C08K 13/02; C08K 3/16; C08K 5/053; C08K 5/07; C08K 5/09; C08K 5/21; C08J 7/0427; C08J 3/226; A61L 29/041
See application file for complete search history.

(56) References Cited

U.S. PATENT DOCUMENTS

| | | | |
|---|---|---|---|
| 7,179,506 B2 | 2/2007 | Chen | |
| 2003/0219594 A1 | 11/2003 | Qin et al. | |
| 2009/0131590 A1 | 5/2009 | Thomas et al. | |
| 2012/0153544 A1 | 6/2012 | Cruz | |

FOREIGN PATENT DOCUMENTS

| | | | |
|---|---|---|---|
| CN | 1803868 | 7/2006 | |
| CN | 101267936 | 9/2008 | |
| CN | 102099419 | 6/2011 | |
| WO | WO-2016142298 A1 * | 9/2016 | ............ A61L 27/34 |

OTHER PUBLICATIONS

Wentao Wang et al., "Effects of various nanomaterials on the properties of starch/poly(vinyl alcohol) composite films formed by blow extrusion process", Iranian Polymer Journal, Aug. 4, 2015, pp. 687-696.
Lale Budi Hutami Rahayu et al., "Synthesis and Characterization of Fe3O4 Nanoparticles using Polyvinyl Alcohol (PVA) as Capping Agent and Glutaraldehyde (GA) as Crosslinker", IOP Conference Series: Materials Science and Engineering, Jan. 1, 2018, pp. 1-8.
A. S. Singha et al., "Effects of plasticizer/cross-linker on the mechanical and thermal properties of starch/PVA blends", Iranian Polymer Journal, Jun. 24, 2014, pp. 655-662.
Xiancai Jiang et al., "The plasticizing mechanism and effect of calcium chloride on starch/poly(vinyl alcohol) films", Carbohydrate Polymers, Nov. 1, 2012, pp. 1677-1684.
Jiaan Yan et al., "Effect of urea and formamide plasticizers on starch/PVA bioblend sheets", Journal of Applied Polymer Science, May 23, 2015, pp. 1-8.
Ravindra V. Gadhave et al., "Effect of glutaraldehyde on thermal and mechanical properties of starch and polyvinyl alcohol blends", Designed Monomers and Polymers, Jan. 1, 2019, pp. 1-8.
Eyyup Karaogul et al., "The Effects of Novel Additives Used in PVA/Starch Biohybrid Films", Fillers—Synthesis, Characterization and Industrial Application, Sep. 28, 2018, pp. 1-17.
"Search Report of Europe Counterpart Application", dated Aug. 13, 2021, p. 1-p. 14.

* cited by examiner

*Primary Examiner* — Edward J Cain
(74) *Attorney, Agent, or Firm* — JCIPRNET

(57) ABSTRACT

The present application discloses a polyvinyl alcohol composition, as well as a preparation method and polyvinyl alcohol medical catheter containing thereof, wherein raw materials include the following components: 60-90 parts of polyvinyl alcohol; 0.1-3 parts of glutaraldehyde; and the polyvinyl alcohol composition is made by mixing the polyvinyl alcohol in molten state with the glutaraldehyde in an acidic environment.

8 Claims, 1 Drawing Sheet

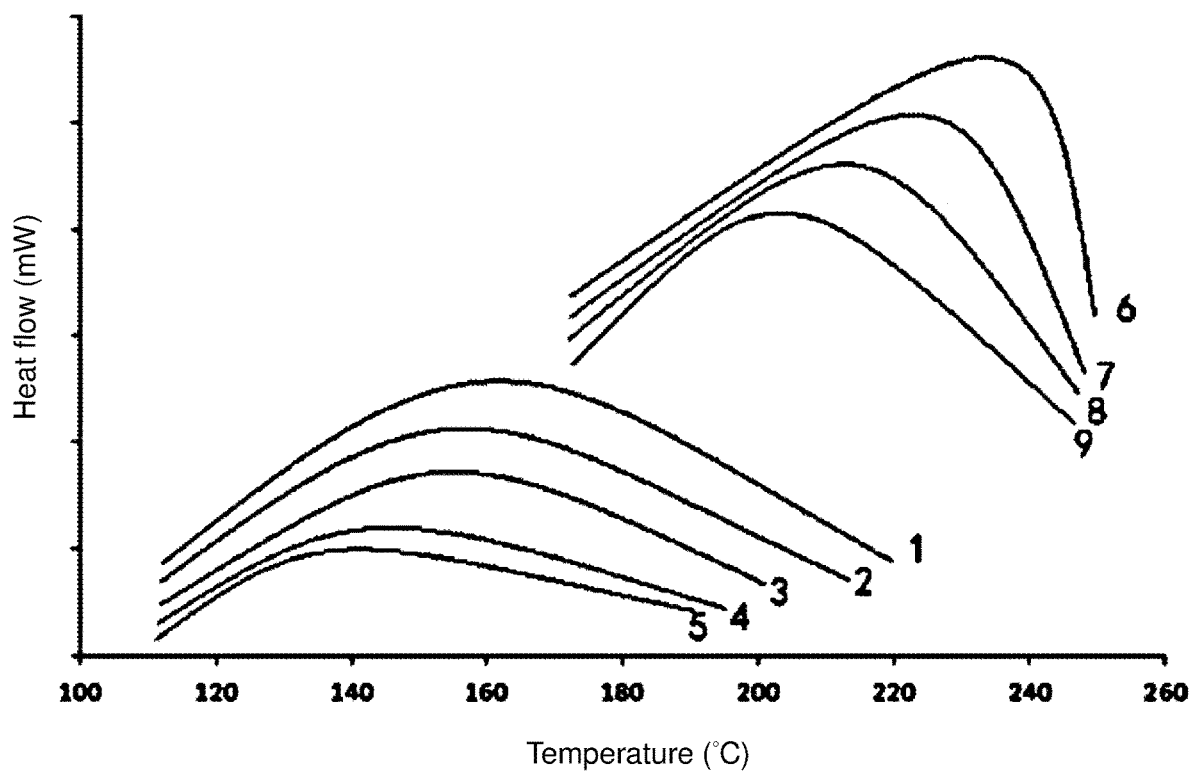

POLYVINYL ALCOHOL COMPOSITION, PREPARATION METHOD THEREOF, AND POLYVINYL ALCOHOL MEDICAL CATHETER CONTAINING THEREOF

CROSS-REFERENCE TO RELATED APPLICATION

This application is a continuation of international application of PCT application serial no. PCT/CN2018/074374, filed on Jan. 27, 2018, which claims the priority benefit of China application no. 201810036428.X, filed on Jan. 15, 2018. The entirety of each of the above mentioned patent applications is hereby incorporated by reference herein and made a part of this specification.

TECHNICAL FIELD

The present application relates to the technical field of macromolecular polymers, in particular to a polyvinyl alcohol composition, a preparation method and polyvinyl alcohol medical catheter containing thereof.

BACKGROUND ART

Polyvinyl alcohol is a polymer having a property between plastics and rubbers. Polyvinyl alcohol has relatively good bonding property, film flexibility, smoothness, oil resistance, solvent protection resistance, and gas barrier property, etc., and polyvinyl alcohol is sanitary and nontoxic, and is biodegradable under certain conditions. Polyvinyl alcohol is widely used in industries such as textile, food, medicine, building, wood processing, paper manufacturing, printing, and agriculture, etc. Among them, medical grade polyvinyl alcohol is safe and nontoxic, non-irritating, non-sensitizing, and cytotoxicity-free to the human body, and has comparatively good biocompatibility, and is one of the ideal materials for the manufacturing of medical devices.

The melting of the high polymer is a process in which the crystalline domain transitions from the crystalline state to the liquid state when the crystalline high polymer is heated, and the temperature at this point is the melting point. The macromolecular long-chain of the high polymer exhibits a certain distribution, and the aggregation state thereof is also a typical two-phase structure, i.e., the crystalline phase and the amorphous phase coexist, therefore, the melting of the high polymer is not very sharp, the melting process occurs in a comparatively wide range, and the temperature at which the melting of the high polymer occurs is called a melting point or a melting temperature.

There are lots of hydroxyl groups in the polyvinyl alcohol molecule, and the hydrogen chain formed from them gives the polyvinyl alcohol comparatively good melting temperature, and the melting temperature is close to the decomposition temperature of the polyvinyl alcohol, which lead to poor processability. It's difficult to perform thermoplastic processing, and the applicability of the polyvinyl alcohol is limited.

SUMMARY OF THE INVENTION

According to an aspect of the invention, there is provided a polyvinyl alcohol composition with the effect of low melting temperature.

The above aspect of the present application is achieved by the technical solution below: a polyvinyl alcohol composition, wherein the raw materials of the polyvinyl alcohol composition include the following components in parts by weight: 60-90 parts of polyvinyl alcohol; 0.1-3 parts of glutaraldehyde; and the polyvinyl alcohol composition is made by mixing the polyvinyl alcohol in molten state with the glutaraldehyde in an acidic environment.

By employing the above technical solution, the polyvinyl alcohol and glutaraldehyde of the raw materials of the polyvinyl alcohol composition undergo cross-linking reaction in the acidic environment to form a three dimensional net structure, which enhance the strength and heat resistance of the polyvinyl alcohol composition. The acidic environment can promote the cross-linking reaction of the glutaraldehyde with the polyvinyl alcohol and increase the decomposition temperature of the polyvinyl alcohol composition, while the melting temperature of the polyvinyl alcohol composition after the cross-linking is decreased, and the processability of the polyvinyl alcohol composition is increased.

Further, the raw materials of the polyvinyl alcohol composition include 4-10 parts of urea by weight.

By employing the above technical solution, since the melting point of the high polymer has a direct relationship with the heat enthalpy and the entropy changes during its melting process, the relationship between the melting point and the heat enthalpy and the entropy changes is: $Tm=\Delta H/\Delta S$, wherein $Tm$ is the melting point of the high polymer, $\Delta H$ is the heat enthalpy change of the high polymer during the melting process, and $\Delta S$ is the entropy change of the high polymer during the melting process. The factors which can influence $\Delta H$ and $\Delta S$ can influence the melting point of the high polymer. Among them, an intermolecular force influences $\Delta H$ and flexibility of the molecular chain influences $\Delta S$. The stronger the intermolecular force is, the larger the molecular bonding force needed to overcome when melting will be, and the higher the melting point of the high polymer will be. Therefore, by adding urea to the raw materials of the polyvinyl alcohol composition and dispersing it in the mixture of the raw materials of the polyvinyl alcohol composition, the intermolecular force between the polyvinyl alcohol molecules is reduced, and the melting point of the polyvinyl alcohol composition is substantially decreased.

Further, the raw materials of the polyvinyl alcohol composition include 5-15 parts of glycerol and 2-10 parts of calcium chloride by weight.

By employing the above technical solution, the raw materials of the polyvinyl alcohol composition include glycerol, which swells and dilutes the polyvinyl alcohol to reduce the intermolecular force between the polyvinyl alcohol molecules, and plays the role of decreasing the melting temperature of the polyvinyl alcohol composition. Also, calcium chloride plays the role of decreasing the melting temperature of the polyvinyl alcohol composition.

Further, the raw materials of the polyvinyl alcohol composition include the following components in parts by weight: 76-85 parts of polyvinyl alcohol; 5.4-6.5 parts of urea; 8-11 parts of glycerol; 3-5 parts of calcium chloride; 0.4-0.6 parts of glutaraldehyde; 0.1-2 parts of acid; the acid is one of 10-98 mass % aqueous solution of the sulfuric acid, aliphatic carboxylic acid, pyrophosphoric acid, and disulfuric acid.

Further, the polyvinyl alcohol has a polymerization degree of 300-7,000, and an alcoholysis degree of 50-99%.

By employing the above technical solution, the polyvinyl alcohol composition of the present application has a low melting temperature. In particular, the lower the polymerization degree of the polyvinyl alcohol is, the lower the melting temperature will be; and the lower the alcoholysis degree of the polyvinyl alcohol is, the lower the melting temperature will be.

According to another aspect of the invention, there is provided a preparation method of polyvinyl alcohol composition, which includes the following steps:

Step 1: polyvinyl alcohol and an acid are mixed and heated at a heating temperature of 140-220° C. to melt the polyvinyl alcohol to obtain an acidic polyvinyl alcohol material, which is pelletized at 140-220° C. to provide pellets;

Step 2: the pellets are uniformly mixed with the glutaraldehyde at 140-220° C. to obtain an intermediate material of the polyvinyl alcohol composition;

Step 3: the intermediate material of the polyvinyl alcohol composition is soaked in 5-10 mass % sodium hydroxide solution for 24-48 hours; and Step 4: the intermediate material of the polyvinyl alcohol composition is taken out of the sodium hydroxide solution and washed with deionized water to obtain the polyvinyl alcohol composition.

Further, in step 1, 4-10 parts of urea, 5-15 parts of glycerol, and 2-10 parts of calcium chloride by weight are added to the mixture of the polyvinyl alcohol and the acid, and the mixture is heated at a heating temperature of 140-220° C. to melt the polyvinyl alcohol to obtain the acidic polyvinyl alcohol material, which is pelletized at 140-220° C. to provide pellets.

According to another aspect of the invention, there is provided a polyvinyl alcohol medical catheter made from a polyvinyl alcohol composition, wherein the material of the polyvinyl alcohol medical catheter is the polyvinyl alcohol composition, and its surface is coated with a coating, and the raw materials of the coating include vinyl pyrrolidone, 2-hydroxyl-4'-(2-hydroxyethoxy)-2-methylpropiophenone, N,N'-methylenebisacrylamide, and ethanol at a mass ratio of 3:1:0.04:95.96.

By employing the above technical solution, the surface of the polyvinyl alcohol medical catheter is coated with a coating, upon which forms a layer of lubricating film when contact with water, that increase the surface lubricity of the polyvinyl alcohol medical catheter. During clinical applications, the lubricating surface of the polyvinyl alcohol medical catheter reduces the stimulation to the cells, doesn't damage the mucous membrane, alleviates the damages to the body cells and tissues, facilitates the operations of a doctor, and relieves the pain of a patient.

Secondly, the surface lubricity of the polyvinyl alcohol medical catheter increases the biocompatibility of the polyvinyl alcohol medical catheter. When the high polymer material without a coating on the surface is exposed to a blood environment, the plasma protein will be rapidly adsorbed onto the surface of the high polymer material, and the adsorbed plasma protein can induce the adhesion, release, and aggregation of platelets, which lead to the formation of thrombi, and on the other hand, can readily activate the coagulation factor in the blood and induce a coagulation reaction. Applying a layer of coating onto the surface of the polyvinyl alcohol medical catheter can reduce the interaction between the surface of the polyvinyl alcohol medical catheter and the plasma protein and blood cells in the blood, exhibiting good anticoagulation performance.

Further, a preparation method of the polyvinyl alcohol medical catheter comprises the following steps:

Step 1: polyvinyl alcohol, glycerol, calcium chloride, an acid, and urea are mixed, extruded with an extruder, and pelletized to provide an acidic polyvinyl alcohol material, wherein the temperature inside the extruder is 140-220° C.;

Step 2: glutaraldehyde and the acidic polyvinyl alcohol material obtained in step 1 are mixed and extruded with an extruder to provide a polyvinyl alcohol pipe, wherein the temperature inside the extruder is 140-220° C.;

Step 3: the polyvinyl alcohol pipe is cooled and soaked in a 5-10 mass % sodium hydroxide solution for 24-48 hours;

Step 4: the polyvinyl alcohol pipe is taken out of the sodium hydroxide solution, washed with deionized water, and cut into a polyvinyl alcohol catheter;

Step 5: the polyvinyl alcohol catheter is coated with a mixed solution and treated with ultraviolet radiation to obtain a polyvinyl alcohol catheter with coating on the surface, the mixed solution including vinyl pyrrolidone, 2-hydroxyl-4'-(2-hydroxyethoxy)-2-methylpropiophenone, N,N'-methylenebisacrylamide, and ethanol;

Step 6: the polyvinyl alcohol catheter with coating on the surface is soaked in an aqueous Artemisia capillaris water-soluble antibacterial solution;

Step 7: the polyvinyl alcohol catheter soaked in the aqueous Artemisia capillaris water-soluble antibacterial solution is taken out and sterilized by radiation; and Step 8: the polyvinyl alcohol catheter subjected to sterilization by radiation is sealed and packaged to provide a finished product of polyvinyl alcohol medical catheter.

According to another aspect of the invention, there is provided the method of using a polyvinyl alcohol composition, wherein the polyvinyl alcohol composition is used to make a sealing gasket, a desiccant, an oil pipe, a handbag, an insole, a packaging bag, or the polyvinyl alcohol composition is mixed with a fertilizer to make a flowerpot.

In summary, the present application has a plurality of beneficial effects. For example, the polyvinyl alcohol composition includes the polyvinyl alcohol, glutaraldehyde, an acid, and urea, etc., and glutaraldehyde undergoes a cross-linking reaction with the polyvinyl alcohol, so that the decomposition temperature of the polyvinyl alcohol composition is increased, while the melting point of the polyethylene alcohol composition is decreased, and the processability of the polyvinyl alcohol composition is enhanced, facilitating a convenient melt processing. The polyvinyl alcohol medical catheter made from the polyvinyl alcohol composition has excellent biocompatibility, and is convenient for clinical operations by a doctor. Furthermore, the polyvinyl alcohol composition can be used to make various articles such as a sealing gasket, a degradable flowerpot, a handbag, etc., making fully use of the performances of the polyvinyl alcohol composition such as low melting temperature, good processability, convenience in melting and processing, excellent biocompatibility, and broad application range.

BRIEF DESCRIPTION OF THE DRAWINGS

FIG. 1 shows DSC test results of examples 1-5 and comparative examples 1-4.

DETAILED DESCRIPTION

Example 1

A polyvinyl alcohol composition having the components of the raw materials shown in table 1 was prepared, in which the acid is aliphatic carboxylic acid, the polymerization degree of the polyvinyl alcohol is 7,000, and the alcoholysis degree is 99%.

The polyvinyl alcohol composition was prepared as follows: step 1: polyvinyl alcohol, glycerol, calcium chloride, and the acid were mixed, extruded with an extruder, and pelletized with a pelletizer to obtain an acidic polyvinyl alcohol material, in which the extruder is a twin screw extruder, the length diameter ratio is 40-60:1, and the temperature inside the extruder is 160-220° C.

Step 2: glutaraldehyde and the acidic polyvinyl alcohol material obtained in step 1 were mixed and extruded with an extruder to obtain an intermediate material of the polyvinyl alcohol composition, in which the temperature inside the extruder is 160-220° C.

Step 3: the intermediate material of the polyvinyl alcohol composition from step 2 was cooled and then soaked in a 5 mass % sodium hydroxide solution for 24-48 hours.

Step 4: the intermediate material of the polyvinyl alcohol composition was taken out of the sodium hydroxide solution and washed with deionized water to obtain the polyvinyl alcohol composition.

Example 2

A polyvinyl alcohol composition having the components of the raw materials shown in table 1 was prepared, in which the acid is pyrophosphoric acid, the polymerization degree of the polyvinyl alcohol is 6,000, and the alcoholysis degree is 80%.

The polyvinyl alcohol composition was prepared as follows: step 1: the polyvinyl alcohol, urea, glycerol, calcium chloride, and the acid were mixed, extruded with an extruder, and pelletized with a pelletizer to obtain an acidic polyvinyl alcohol material, in which the extruder is a twin screw extruder, the length diameter ratio is 40-60:1, and the temperature inside the extruder is 150-180° C.

Step 2: glutaraldehyde and the acidic polyvinyl alcohol material obtained in step 1 were mixed and extruded with an extruder to obtain an intermediate material of the polyvinyl alcohol composition, in which the temperature inside the extruder is 150-180° C.

Step 3: the intermediate material of the polyvinyl alcohol composition from step 2 was cooled and then soaked in a 8 mass % sodium hydroxide solution for 24-48 hours.

Step 4: the intermediate material of the polyvinyl alcohol composition was taken out of the sodium hydroxide solution and washed with deionized water to obtain the polyvinyl alcohol composition.

Example 3

A polyvinyl alcohol composition having components of the raw materials of the polyvinyl alcohol composition shown in table 1 was prepared, in which the acid is disulfuric acid, the polymerization degree of the polyvinyl alcohol is 4,000, and the alcoholysis degree is 70%.

Example 4

A polyvinyl alcohol composition having the components of the raw materials shown in table 1 was prepared, in which the acid is 10 mass % sulfuric acid aqueous solution, the polymerization degree of the polyvinyl alcohol is 2,000, and the alcoholysis degree is 50%.

The polyvinyl alcohol composition was prepared as follows: step 1: the polyvinyl alcohol, urea, glycerol, calcium chloride, and the acid were mixed, extruded with an extruder, and pelletized with a pelletizer to obtain an acidic polyvinyl alcohol material, in which the extruder is a twin screw extruder, the length diameter ratio is 40-60:1, and the temperature inside the extruder is 140-160° C.

Step 2: glutaraldehyde and the acidic polyvinyl alcohol material obtained in step 1 were mixed and extruded with an extruder to obtain an intermediate material of the polyvinyl alcohol composition, in which the temperature inside the extruder is 140-160° C.

Step 3: the intermediate material of the polyvinyl alcohol composition from step 2 was cooled and then soaked in a 10 mass % sodium hydroxide solution for 24-48 hours.

Step 4, the intermediate material of the polyvinyl alcohol composition was taken out of the sodium hydroxide solution and washed with deionized water to obtain the polyvinyl alcohol composition.

Example 5

A polyvinyl alcohol composition was prepared, differing from example 4 in that, the components of the raw materials of the polyvinyl alcohol are as shown in table 1, in which the acid is a 98 mass % sulfuric acid aqueous solution. The polymerization degree of the polyethylene is 300, and the alcoholysis degree is 50%. In preparing the polyethylene composition, the temperature inside the extruder in step 1 is 140-220° C., and the temperature inside the extruder in step 2 is 140-220° C.

Example 6

A polyvinyl alcohol medical catheter made of a polyvinyl alcohol composition was prepared. The raw materials of the polyvinyl alcohol composition include the components as shown in table 1, in which the acid is a 60 mass % sulfuric acid aqueous solution, the polymerization degree of the polyvinyl alcohol is 300-7,000, and the degree of alcoholysis is 50-99%. The material of the polyvinyl alcohol medical catheter is the polyvinyl alcohol composition, and it's surface is coated with a coating, and the raw materials of the coating included vinyl pyrrolidone, 2-hydroxyl-4'-(2-hydroxyethoxy)-2-methylpropiophenone, N,N'-methylenebisacrylamide, and ethanol.

The polyvinyl alcohol medical catheter was prepared as follows: step 1: polyvinyl alcohol, glycerol, calcium chloride, the acid, and urea were mixed, extruded with an extruder, and pelletized to obtain an acidic polyvinyl alcohol material, wherein the extruder is a twin screw extruder, the length diameter ratio of the screw is 40-60:1, and the temperature inside the extruder is 140-220° C.

Step 2: glutaraldehyde and the acidic polyvinyl alcohol material obtained in step (1) were mixed and extruded with an extruder to obtain a polyvinyl alcohol pipe, wherein the temperature inside the extruder is 140-220° C.

Step 3: the polyvinyl alcohol pipe was cooled and then soaked in a 5-10 mass % sodium hydroxide solution for 24-48 hours.

Step 4: the polyvinyl alcohol pipes was taken out of the sodium hydroxide solution, washed with deionized water, and cut into a polyvinyl alcohol catheter.

Step 5: the polyvinyl alcohol catheter was coated with a mixed solution and treated with ultraviolet radiation to obtain a polyvinyl alcohol catheter with coating on the surface, in which the mixed solution include vinyl pyrrolidone, 2-hydroxyl-4'-(2-hydroxyethoxy)-2-methylpropiophenone, N,N'-methylenebisacrylamide, and ethanol, where the mass ratio of the components of the mixed solution was: vinyl pyrrolidone:2-hydroxyl-4'-(2-hydroxyethoxy)-2-methylpropiophenone:N,N'-methylenebisacrylamide:ethanol=3:1:0.04:95.96. The range of the ultraviolet wavelength during the treatment with ultraviolet radiation is 365-370 nm.

Step 6: the polyvinyl alcohol catheter with coating on the surface was soaked in an aqueous Artemisia capillaris water-soluble antibacterial solution.

Step 7: the polyvinyl alcohol catheter soaked in the aqueous Artemisia capillaris water-soluble antibacterial solution was taken out and sterilized with radiation, wherein cobalt 60 is used for the sterilization with radiation, and the radiant quantity is 0.5-1.5 KGy.

Wherein, each of the 100 ml of the aqueous Artemisia capillaris water-soluble antibacterial solution was prepared as follows: a: 10 g of material, that is, a whole plant of the Artemisia capillaris, was weighed and added into an Erlenmeyer flask; b: adding water: 150 g of distilled water was added into the Erlenmeyer flask; c: leaching: the Erlenmeyer flask was thermostatically treated at 60° C. for 80 minutes; d: bringing to volume: the mixture in the Erlenmeyer flask was poured into a volumetric flask through a funnel, then water was added into the volumetric flask to the volume of 500 mL, and the mixture was shaken multiple times and let stand for 10 minutes; e, filtering: the mixture was filtered with a funnel to obtain 100 mL of filtrate, i.e., the aqueous Artemisia capillaris water-soluble antibacterial solution.

Step 8: the polyvinyl alcohol catheter subjected to sterilization with radiation was sealed and packaged to obtain a finished product of the polyvinyl alcohol medical catheter.

Example 7

A sealing gasket was made from any of the polyvinyl alcohol compositions of examples 1-5. The polyvinyl alcohol composition was injected by using a plastic injection molding machine into a mold so as to be shaped into a sealing gasket. Since the polyvinyl alcohol has the water absorbency, the sealing gasket swells after absorption of water, which increases the sealing property of the sealing gasket.

Example 8

A desiccant was made from any of the polyvinyl alcohol compositions of examples 1-5. The preparation method was as follows: the polyvinyl alcohol composition was cut into pieces to obtain a desiccant. The polyvinyl alcohol in the desiccant has water absorbency, so that it absorbs water and provides a good drying effect.

Example 9

An oil pipe was made from any of the polyvinyl alcohol compositions of examples 1-5. The preparation method of the oil pipe was as follows: step 1: the polyvinyl alcohol, glycerol, calcium chloride, the acid, and urea are mixed, extruded with an extruder, and pelletized to obtain an acidic polyvinyl alcohol material, wherein the extruder is a twin screw extruder, the length diameter ratio of the screw is 40-60:1, and the temperature inside the extruder is 140-220° C.

Step 2: glutaraldehyde and the acidic polyvinyl alcohol material obtained in step 1) were mixed and extruded with an extruder to obtain a polyvinyl alcohol pipe, wherein the temperature inside the extruder is 140-220° C.

Step 3: the polyvinyl alcohol pipes were cooled and then soaked in a 5-10 mass % sodium hydroxide solution for 24-48 hours.

Step 4: the polyvinyl alcohol pipe was taken out of the sodium hydroxide solution, washed with deionized water, and cut into an oil pipe. The oil pipe obtained has the advantages of good air barrier property and smooth inner wall.

Example 10

A handbag was made from any of the polyvinyl alcohol compositions of examples 1-5, wherein the handbag was made by a blow molding process. The handbag as obtained is susceptible to degradation in the environment after usage.

Example 11

An insole was made from any of the polyvinyl alcohol compositions of examples 1-5, in which the polyvinyl alcohol composition was injected into a mold by a plastic injection molding machine to be shaped into an insole. The raw materials of the insole contain the polyvinyl alcohol having water absorbency, therefore the insole has the ability of absorbing sweat.

Example 12

A flowerpot was made by mixing any of the polyvinyl alcohol compositions of examples 1-5 with a fertilizer. During the manufacturing the polyvinyl alcohol composition was heated to 140-220° C. The fertilizer was added and stirred until becoming homogeneous, and the mixture was poured into a mold so as to be cooled and shaped into a flowerpot. During using the flowerpot, the polyvinyl alcohol was continuously degraded, and thus the fertilizer contained in the flowerpot was continuously released to provide nutrients for the plant in the flowerpot.

Example 13

A packaging bag was made from any of the polyvinyl alcohol compositions of examples 1-5, in which the packaging bag was made by a blow molding process. The packaging bag thus obtained is susceptible to degradation in the environment after use.

Comparative Example 1

A polyvinyl alcohol with a polymerization degree of 300-7000 and an alcoholysis degree of 50%-99%.

Comparative Example 2

A polyvinyl alcohol composition with the components of the raw materials shown in table 1, in which the polymerization degree of the polyvinyl alcohol is 300-7000, and the alcoholysis degree is 50%-99%.

The polyvinyl alcohol composition was prepared as follows: step 1: the polyvinyl alcohol, glycerol, and calcium chloride were mixed, extruded with an extruder, and pelletized with a pelletizer to obtain a polyvinyl alcohol material, wherein the extruder is a twin screw extruder, the length diameter ratio is 40-60:1, and the temperature inside the extruder is 140-220° C.

Step 2: glutaraldehyde and the polyvinyl alcohol material obtained in step 1 were mixed and extruded with an extruder to obtain a polyvinyl alcohol composition, in which the temperature inside the extruder was 140-220° C.

Comparative Example 3

A polyvinyl alcohol composition with the components of the raw materials as shown in table 1, in which the polymerization degree of the polyvinyl alcohol is 3007000, and the alcoholysis degree is 50%-99%.

The polyvinyl alcohol composition was prepared as follows: the polyvinyl alcohol, glycerol, and calcium chloride were mixed, extruded with an extruder, and pelletized with a pelletizer to obtain an acidic polyvinyl alcohol material, wherein the extruder is a twin screw extruder, the length diameter ratio is 40-60:1, and the temperature inside the extruder is 140-220° C. The acidic polyvinyl alcohol material was pelletized to provide a polyvinyl alcohol composition.

Comparative Example 4

A polyvinyl alcohol composition with the components of the raw materials as shown in table 1, in which the polymerization degree of the polyvinyl alcohol is 3007000, and the alcoholysis degree is 50%-99%.

The polyvinyl alcohol composition was prepared as follows: the polyvinyl alcohol, urea, glycerol, and calcium chloride were mixed, extruded with an extruder, and pelletized with a pelletizer to obtain an acidic polyvinyl alcohol composition, in which the extruder is a twin screw extruder, the length diameter ratio is 40-60:1, and the temperature inside the extruder is 140-220° C. The acidic polyvinyl alcohol composition was pelletized to obtain the polyvinyl alcohol composition.

TABLE 1

| | Polyvinyl alcohol (Kg) | Urea (Kg) | Glycerol (Kg) | Calcium chloride (Kg) | Glutaraldehyde (Kg) | Acid (Kg) |
|---|---|---|---|---|---|---|
| Example 1 | 76 | 0 | 8 | 3 | 0.4 | 0.1 |
| Example 2 | 76 | 5.4 | 8 | 3 | 0.4 | 0.1 |
| Example 3 | 85 | 6.5 | 11 | 5 | 0.6 | 0.6 |
| Example 4 | 60 | 10 | 5 | 10 | 0.1 | 1 |
| Example 5 | 90 | 4 | 15 | 2 | 3 | 2 |
| Example 6 | 85 | 6.5 | 11 | 5 | 0.6 | 0.6 |
| Comparative Example 2 | 76 | 0 | 8 | 3 | 0.4 | 0 |
| Comparative Example 3 | 76 | 0 | 8 | 3 | 0 | 0 |
| Comparative Example 4 | 76 | 5.4 | 8 | 3 | 0 | 0 |

The polyvinyl alcohol composition was test regarding the melting temperature: The polyvinyl alcohol compositions of examples 1-5 and comparative examples 1-4 and the polyvinyl alcohol of comparative example 1 were subjected to a DSC test, that is, Differential Scanning Calorimetry test, respectively. The test results are shown in FIG. 1, wherein curve 1 is the test result of example 1, curve 2 is the test result of example 2, curve 3 is the test result of example 3, curve 4 is the test result of example 4, curve 5 is the test result of example 5, curve 6 is the test result of comparative example 1, curve 7 is the test result of comparative example 3, curve 8 is the test result of comparative example 4, and curve 9 is the test result of comparative example 2. The results of FIG. 1 show that all the melting points of the polyvinyl alcohol composition of examples 1-6 are apparently lower than the melting points of the polyvinyl alcohol of comparative example 1 and the polyvinyl alcohol composition of comparative examples 2-4.

What is claimed is:

1. A polyvinyl alcohol composition, wherein raw materials of the polyvinyl alcohol composition comprise the following components in parts by weight: 60-90 parts of polyvinyl alcohol; and 0.1-3 parts of glutaraldehyde; and the polyvinyl alcohol composition is made by mixing the polyvinyl alcohol in molten state with the glutaraldehyde in an acidic environment.

2. The polyvinyl alcohol composition according to claim 1, wherein the raw materials of the polyvinyl alcohol composition further comprise 4-10 parts of urea by weight.

3. The polyvinyl alcohol composition according to claim 2, wherein the raw materials of the polyvinyl alcohol composition further comprise 5-15 parts of glycerol and 2-10 parts of calcium chloride by weight.

4. The polyvinyl alcohol composition according to claim 3, wherein the raw materials of the polyvinyl alcohol composition comprise the following components in parts by weight: 76-85 parts of polyvinyl alcohol; 5.4-6.5 parts of urea; 8-11 parts of glycerol; 3-5 parts of calcium chloride; 0.4-0.6 part of glutaraldehyde; 0.1-2 parts of acid; wherein the acid is one of a 10-98 mass % sulfuric acid aqueous solution, an aliphatic carboxylic acid, pyrophosphoric acid, and disulfuric acid.

5. The polyvinyl alcohol composition according to claim 1, wherein a polymerization degree of the polyvinyl alcohol is 300-7,000, and an alcoholysis degree of the polyvinyl alcohol is 50-99%.

6. A preparation method of the polyvinyl alcohol composition according to claim 1, comprising:
   step 1: mixing polyvinyl alcohol with the acid, heating at a heating temperature of 140-220° C. to melt the polyvinyl alcohol to obtain an acidic polyvinyl alcohol material, and then pelletizing the acidic polyvinyl alcohol material at 140-220° C. to provide pellets;
   step 2: uniformly mixing the pellets with glutaraldehyde at 140-220° C. to obtain an intermediate material of the polyvinyl alcohol composition;
   step 3: soaking the intermediate material of the polyvinyl alcohol composition in a 5-10 mass % sodium hydroxide solution for 24-48 hours; and
   step 4: taking the intermediate material of the polyvinyl alcohol composition out of the sodium hydroxide solution and washing with deionized water to obtain the polyvinyl alcohol composition.

7. The preparation method of the polyvinyl alcohol composition according to claim 6, wherein in step 1, 4-10 parts of urea, 5-15 parts of glycerol, and 2-10 parts of calcium chloride are added to the mixture of the polyvinyl alcohol and the acid before heating.

8. A polyvinyl alcohol medical catheter, wherein the polyvinyl alcohol medical catheter is made from the polyvinyl alcohol composition of claim 4, and a surface of the polyvinyl alcohol medical catheter is coated with a coating comprising vinyl pyrrolidone, 2-hydroxyl-4'-(2-hydroxyethoxy)-2-methylpropiophenone, N,N'-methylenebisacrylamide, and ethanol at a mass ratio of vinyl pyrrolidone,2-hydroxyl-4'-(2-hydroxyethoxy)-2-methylpropiophenone,N, N'-methylenebisacrylamide and ethanol of 3:1:0.04:95.96.

* * * * *